United States Patent
O'Hagan et al.

(10) Patent No.: US 7,501,134 B2
(45) Date of Patent: Mar. 10, 2009

(54) MICROPARTICLES WITH ADSORBED POLYPEPTIDE-CONTAINING MOLECULES

(75) Inventors: Derek O'Hagan, Berkeley, CA (US); Manmohan Singh, San Ramon, CA (US); Jina Kazzaz, San Rafael, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 315 days.

(21) Appl. No.: 10/505,250

(22) PCT Filed: Feb. 20, 2003

(86) PCT No.: PCT/US03/05017

§ 371 (c)(1), (2), (4) Date: May 13, 2005

(87) PCT Pub. No.: WO03/070909

PCT Pub. Date: Aug. 28, 2003

(65) Prior Publication Data

US 2005/0220883 A1   Oct. 6, 2005

Related U.S. Application Data

(60) Provisional application No. 60/358,315, filed on Feb. 20, 2002.

(51) Int. Cl.
- A61K 9/14 (2006.01)
- A61K 9/48 (2006.01)
- A61K 9/50 (2006.01)
- A61K 47/00 (2006.01)
- A61K 39/00 (2006.01)
- A61K 38/00 (2006.01)

(52) U.S. Cl. .................. 424/489; 424/450; 424/490; 424/184.1; 424/278.1; 424/491; 514/2

(58) Field of Classification Search .............. None
See application file for complete search history.

(56) References Cited

U.S. PATENT DOCUMENTS

| | | | |
|---|---|---|---|
| 5,858,410 A | 1/1999 | Muller et al. | |
| 6,207,646 B1 * | 3/2001 | Krieg et al. | 514/44 |
| 6,383,470 B1 | 5/2002 | Fritzsch et al. | |
| 2002/0136776 A1 | 9/2002 | Fang et al. | |
| 2005/0107322 A1 | 5/2005 | O'Hagan et al. | 514/44 |

FOREIGN PATENT DOCUMENTS

| WO | WO 94/27718 | * 12/1994 |
|---|---|---|
| WO | WO 97/02810 | 1/1997 |
| WO | WO 98/33487 | 8/1998 |
| WO | WO 00/06123 | 2/2000 |
| WO | WO 00/50006 | 8/2000 |
| WO | WO 01/36599 | 5/2001 |
| WO | WO 01/81609 | 11/2001 |
| WO | WO 02/26209 | 4/2002 |
| WO | WO 02/26212 | 4/2002 |
| WO | WO 2004/032958 | * 4/2004 |

OTHER PUBLICATIONS

Pizza et al., "Identification of vaccine candidates against serogroup B meningococcus by whole-genome sequencing," Science, vol. 287 No. 5459, pp. 1816-1820 (Mar. 2000).*

Constantino et al., "Size fractionation of bacterial capsular polysaccharides for their use in conjugate vaccines," Vaccine, vol. 17 No. 9-10, pp. 1251-1263 (Mar. 1999).*

M. Briones et al., "The Preparation, Characterization, and Evaluation of Cationic Microparticles for DNA Vaccine Therapy," *Pharmaceutical Research*, 18(5):709-712 (2001).

J. Kazzaz et al, "Novel Anionic Microparticles Are a Potent Adjuvant for the Induction of Cytoxic T Lymphocytes Against Recombinant p55 Gag from HIV -1," *J. Controlled Release*, 67:347-356 (2000).

K.S. Denis-Mize et al., "Plasmid DNA Adsorbed onto Cationic Microparticles Mediates Target Gene Expression and Antigen Presentation by Dendritic Cells," *Gene Therapy*, 7:2105-2112 (2000).

H. Jeffrey et al., "The Preparation and Characterization of Poly(lactide-co-glycolide) Microparticles. II. The Entrapment of a Model Protein Using a (Water-in-Oil)-in-Water Emulsion Solvent Evaporation Technique," *Pharmaceutical Research*, 10(3):362-368 (1993).

(Continued)

*Primary Examiner*—Zachariah Lucas
(74) *Attorney, Agent, or Firm*—Helen Lee; Otis Littlefield; Robert Gorman

(57) ABSTRACT

Microparticles with absorbed polypeptide-containing molecules formed without the use of surfactant, methods of making such microparticle compositions, and uses thereof, are disclosed. The microparticles comprise a polymer, such as a poly(α-hydroxy acid), a polyhydroxy butyric acid, a polycaprolactone, a polyorthoester, a polyanhydride, and the like. Preferred polymers are poly(D,L-lactide-co-glycolides), more preferable those having a lactide/glycolide molar ratio ranging from 40:60 to 60:40 and having a molecular weight ranging from 20,000 Daltons to 70,000 Daltons. Preferred polypeptide containing molecules are bacterial and viral antigens (including HIV antigens, meningitis B antigens, streptococcus B antigens, and Influenza A hemagglutinin antigens).

41 Claims, 1 Drawing Sheet

OTHER PUBLICATIONS

D.T. O'Hagan et al., "Long-Term Antibody Responses in Mice Following Subcutaneous Immunization with Ovalbumin Entrapped in Biodegradable Microparticles," *Vaccine*, 11(9):965-969 (1993).

M. Singh et at, "Cationic Microparticles Are an Effective Delivery System for Immune Stimulatory CpG DNA," *Pharmaceutical Research*, 18(10):1476-1479 (2001).

M. Singh et al., "Cationic Microparticles: A Potent Delivery System for DNA Vaccines," *Proc. Natl Acad. Sci. USA*, 97(2):811-816 (2000).

M. Singh et al., "Mucosal Immunization with HIV-1 Gag DNA on Cationic Microparticles Prolongs Gene Expression and Enhances Local and Systemic Immunity," *Vaccine*, 20:594-602 (2002).

D. O'Hagan et al, "Induction of Potent Immune Responses by Cationic Microparticles with Adsorbed Human Immunodeficiency Virus DNA Vaccines," *J. Virol.*, 75(19):9037-9043 (2001).

Y.-I. Jeong et al., "Preparation of poly(DL-lactide-co-glycolide) nanoparticles without surfactant," *J. Appl. Polymer Sci.*, 80:2228-2236 (2001).

H.-J. Jeon et al., "Effect of solvent on the preparation of surfactant-free poly(DL-lactide-co-glycolide) nanoparticles and norfloxacin release characteristics," *Int. J. Pharm.*, 207:99-108 (2000).

I. Soriano et al., "Use of surfactants in polylactic acid protein microspheres," *Drug Develop. Indust. Pharm.*, 21(5):549-558 (1995).

C.-Y. Yang et al., "En capsulating aspirin into a surfactant-free ethyl cellulose microsphere using non-toxic solvents by emulsion solvent-evaporation technique," *J. Microencapsulation*, 18(2):223-236 (2001).

Y. Kawashima et al., "Pro perties of a peptide containing DL-lactide/glycolide copolymer nanospheres prepared by novel emulsion solvent diffusion methods," *Eur. J. Pharm.*, 45:41-48 (1998).

J.-C. Olivier et al., "Preparation and Characterization of Biodegradable poly(isobutylcyano acrylate) Nanoparticles with the Surface Modified by the Adsorption of Proteins", *Colloids and Surfaces B: Biointerfaces*, vol. 4, 1995, pp. 349-356.

Yasemin Ataman-Önal et al., "Surfactant-Free Anionic PLA Nanoparticles Coated with HIV-1 p24 Protein Induced Cellular and Humoral Immune Responses in Various Animal Models," *Journal of Controlled Release*, vol. 112, 2006, pp. 175-185.

Delphine Lamalle-Bernard et al., "Coadsorption of HIV-1 p24 and gp120 Proteins to Surfactant-Free Anionic PLA Nanoparticles Preserves Antigenicity and Immunogenicity", *Journal of Controlled Release*, vol. 115, 2006, pp. 57-67.

A.Carrio et al., "Preparation and Degradation of Surfactant-Free PLAGA Microspheres", *Journal of Controlled Release*, vol. 37, 1995, pp. 113-121.

\* cited by examiner

MICROPARTICLES WITH ADSORBED POLYPEPTIDE-CONTAINING MOLECULES

STATEMENT OF RELATED APPLICATION

This application is a 371 of PCT/US03/05017, filed Feb. 20, 2003, claims the benefit of U.S. Provisional Patent Application Ser. No. 60/358,315, filed Feb. 20, 2002, entitled "Microparticles With Adsorbed Polypeptide-Containing Molecules," each of which is hereby incorporated by reference.

TECHNICAL FIELD

The present invention relates generally to pharmaceutical compositions. In particular, the invention relates to biodegradable microparticles with adsorbed polypeptide-containing molecules that are formed without the use of surfactant, methods for preparing such microparticles, and uses thereof.

BACKGROUND

Particulate carriers have been used with adsorbed or entrapped antigens in attempts to elicit adequate immune responses. Such carriers present multiple copies of a selected antigen to the immune system and promote trapping and retention of antigens in local lymph nodes. The particles can be phagocytosed by macrophages and can enhance antigen presentation through cytokine release.

For example, commonly owned International patent application WO 98/33487 (PCT/US98/01738) and co-pending U.S. patent application Ser. No. 09/015,652, filed Jan. 29, 1998, describe the use of antigen-adsorbed and antigen-encapsulated microparticles to stimulate immunological responses, including cell-mediated immunological responses, as well as methods of making the microparticles. Polymers used to form the microparticles include poly(lactide) and poly(lactide-co-glycolide), also referred to herein as "PLG".

Commonly owned International patent application WO 00/06123 (PCT/US99/17308) and co-pending U.S. patent application Ser. No. 09/715,902 disclose methods of making microparticles having adsorbed macromolecules, including polynucleotides and polypeptide antigens. The microparticles comprise, for example, a polymer such as a poly(alpha-hydroxy acid) (e.g., PLG, a polyhydroxy butyric acid, a polycaprolactone, a polyorthoester, a polyanhydride, and the like) and are formed using, for example, cationic, anionic or nonionic detergents. Microparticles containing anionic detergents, such as PLG microparticles with sodium dodecyl sulfate (SDS), are proposed for the use of positively charged macromolecules, such as polypeptides. Microparticles containing cationic detergents, such as PLG microparticles with CTAB (also known as cetrimide or cetyl trimethyl ammonium bromide), are proposed for the use of negatively charged macromolecules, such as DNA. The use of such microparticles to stimulate immunological responses, including cell-mediated immunological responses, is also disclosed.

In each of the above references, however, one or more surfactants are utilized during preparation of the macromolecule-adsorbed microparticles. Unfortunately, the use of surfactants can raise toxicological issues that result in additional regulatory scrutiny during product registration, among other consequences.

SUMMARY OF THE INVENTION

The present inventors have unexpectedly found that microparticles with adsorbed polypeptide-containing molecules can be formed in the absence of a surfactant.

For instance, according to a first aspect of the invention, a biologically active microparticle composition is provided, which comprises: (a) microparticles comprising a polymer selected from the group consisting of a poly($\alpha$-hydroxy acid), a polyhydroxy butyric acid, a polycaprolactone, a polyorthoester, a polyanhydride, and a polycyanoacrylate; and (b) a polypeptide-containing molecule, which is adsorbed to the microparticles. The composition is formed in the absence of anionic surfactant, and is preferably formed in the absence of all surfactants, including anionic, cationic, nonionic and zwitterionic surfactants.

Preferred polymers are poly($\alpha$-hydroxy acids), more preferably those selected from the group consisting of poly(L-lactide), poly(D,L-lactide) and poly(D,L-lactide-co-glycolide). More preferred are poly(D,L-lactide-co-glycolide) polymers. Preferred poly(D,L-lactide-co-glycolide) polymers are those having a lactide/glycolide molar ratio ranging from 25:75 to 75:25, more preferably 40:60 to 60:40, and having a molecular weight ranging from 10,000 to 100,000 Daltons, more preferably from 30,000 Daltons to 70,000 Daltons.

Preferred biologically active polypeptide-containing molecules include bacterial and viral antigens. HIV antigens (such as g41, gp120, gp140, p24gag and p55gag antigens), meningitis B antigens (such as meningitis B recombinant protein 287 antigen), streptococcus antigens (such as group B streptococcus antigen), and Influenza A hemagglutinin antigens are particularly preferred.

In some embodiments, the microparticle composition is provided with a further biologically active macromolecule, which may be bound or unbound to the microparticles, and may even be entrapped within the polymer. For example, the microparticle composition may be provided with an adjuvant, particularly a Th1 stimulating adjuvant. Preferred adjuvants include CpG oligonucleotides, LTK63, LTR72, MPL, aminoalkyl glucosaminide 4-phosphates (AGP's), imidazoquinoline adjuvants, lipopolysaccharide mimetic adjuvants, QS21, double-stranded RNA (dsRNA) and aluminum salts, including aluminum phosphate.

According to another aspect of the present invention, a pharmaceutically acceptable excipient is added to the above microparticle compositions.

Another aspect of the invention is directed to the delivery of a polypeptide-containing molecule to a vertebrate subject, which comprises administering to a vertebrate subject the above microparticle composition.

In other aspects of the invention, the above microparticle compositions are used in the diagnosis of diseases, in the treatment of diseases, in vaccines, and/or in raising an immune response.

For example, in an additional aspect, the invention is directed to a method for eliciting a cellular and/or humoral immune response in a vertebrate subject, which comprises administering to a vertebrate subject a therapeutically effective amount of a microparticle composition as described above.

Another aspect of the invention is directed to a method of immunization, which comprises administering to a vertebrate subject a therapeutically effective amount of the microparticle composition above.

Still other aspects of the invention are directed to methods of producing microparticles. In general, these methods comprise: (a) forming an emulsion comprising (i) a polymer selected from the group consisting of a poly(α-hydroxy acid), a polyhydroxy butyric acid, a polycaprolactone, a polyorthoester, a polyanhydride, and a polycyanoacrylate, (ii) an organic solvent, and (iii) water; followed by (b) removal of the organic solvent The method is carried out using compositions that are free of anionic surfactant, and are preferably free of all surfactant, including anionic, cationic, nonionic and zwitterionic surfactants.

Preferably, the emulsion is a water-in-oil-in-water emulsion that is formed by a process comprising: (a) emulsifying an organic phase comprising polymer and organic solvent with a first aqueous phase comprising water to form a water-in-oil emulsion; and (b) emulsifying a second aqueous phase comprising water with the emulsion formed in step (a) to form a water-in-oil-in-water emulsion. In general, these microparticle compositions are subsequently intermixed with a biologically active polypeptide-containing molecule, such as those discussed above, to produce a biologically active composition.

Although double-emulsion techniques like that above are preferred, single emulsion techniques can also be used to form the microparticle compositions of the present invention.

Still other aspects of the invention are directed to methods of producing microparticle compositions, which methods comprise: (1) forming a microparticle in an emulsification process, which microparticle comprises a polymer selected from the group consisting of a poly(α-hydroxy acid), a polyhydroxy butyric acid, a polycaprolactone, a polyorthoester, a polyanhydride, and a polycyanoacrylate; and (2) adsorbing a biologically active polypeptide-containing molecule on the surface of the microparticle. The method is carried out using compositions that are free of anionic surfactant, and are preferably free of all surfactant, including anionic, cationic, nonionic and zwitterionic surfactants.

An advantage of the present invention is that microparticle compositions for human administration, and particularly microparticle compositions for human administration that contain adsorbed polypeptide-containing molecules, can be formed without resorting to the use of surfactants. The absence of surfactants is beneficial, inter alia, because the addition of surfactants raises issues of toxicity, which issues are circumvented by the microparticle compositions of the present invention.

These and other embodiments, aspects and advantages of the present invention will readily occur to those of ordinary skill in the art in view of the disclosure herein.

DETAILED DESCRIPTION OF THE INVENTION

Figure 1:
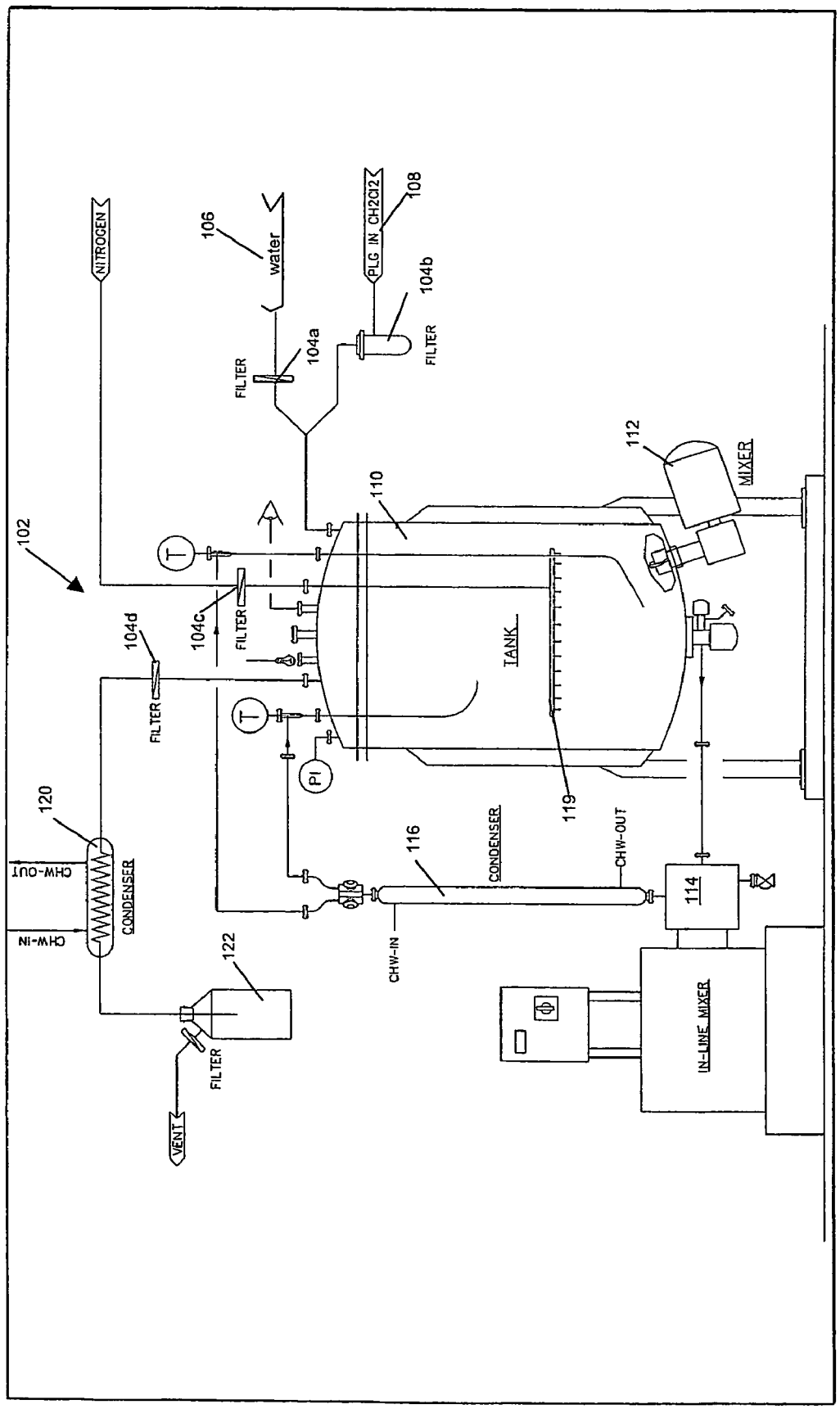
FIG. 1 is a schematic diagram of an apparatus appropriate for producing the microparticle compositions of the present invention.

The practice of the present invention will employ, unless otherwise indicated, conventional methods of chemistry, polymer chemistry, biochemistry, molecular biology, immunology and pharmacology, within the skill of the art. Such techniques are explained fully in the literature. See, e.g., *Remington's Pharmaceutical Sciences,* 18th Edition (Easton, Pa.: Mack Publishing Company, 1990); *Methods In Enzymology* (S. Colowick and N. Kaplan, eds., Academic Press, Inc.); *Handbook of Experimental Immunology,* Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Handbook of Surface and Colloidal Chemistry* (Birdi, K. S., ed, CRC Press, 1997) and *Seymour/Carraher's Polymer Chemistry* (4th edition, Marcel Dekker Inc., 1996).

All publications, patents and patent applications cited herein, whether supra or infra, are hereby incorporated by reference in their entirety.

As used in this specification, the singular forms "a," "an" and "the" include plural references unless the content clearly dictates otherwise. Thus, for example, the term "microparticle" refers to one or more microparticles, and the like.

A. Definitions

In describing the present invention, the following terms will be employed, and are intended to be defined as indicated below.

Unless stated otherwise, all percentages and ratios herein are given on a weight basis.

The term "microparticle" as used herein, refers to a particle of about 10 nm to about 150 μm in diameter, more preferably about 200 nm to about 30 μm in diameter, and most preferably about 500 nm to about 10 μm in diameter. Preferably, the microparticle will be of a diameter that permits parenteral or mucosal administration without occluding needles and capillaries. Microparticle size is readily determined by techniques well known in the art, such as photon correlation spectroscopy, laser diffractometry and/or scanning electron microscopy. The term "particle" may also be used to denote a microparticle as defined herein.

Polymer microparticles for use herein are formed from materials that are sterilizable, non-toxic and biodegradable. Such materials include, without limitation, poly(α-hydroxy acid), polyhydroxybutyric acid, polycaprolactone, polyorthoester, polyanhydride, PACA, and polycyanoacrylate. Preferably, microparticles for use with the present invention are polymer microparticles derived from a poly(α-hydroxy acid), in particular, from a poly(lactide) ("PLA") or a copolymer of D,L-lactide and glycolide or glycolic acid, such as a poly(D,L-lactide-co-glycolide) ("PLG"), or a copolymer of D,L-lactide and caprolactone. The polymer microparticles may be derived from any of various polymeric starting materials which have a variety of molecular weights and, in the case of the copolymers such as PLG, a variety of lactide: glycolide ratios, the selection of which will be largely a matter of choice, depending in part on the coadministered polypeptide-containing molecule. These parameters are discussed more fully below.

The term "surfactant" as used herein includes detergents, dispersing agents, suspending agents, and emulsion stabilizers. Anionic surfactants that have been proposed in the past for use in microparticle formulations include, but are not limited to, SDS (sodium dodecyl sulfate), SLS (sodium lauryl sulfate), DSS (disulfosuccinate), sulphated fatty alcohols, and the like. Cationic surfactants that have been proposed include, but are not limited to, cetrimide (cetyl trimethyl ammonium bromide, or "CTAB"), benzalkonium chloride, DDA (dimethyl dioctodecyl ammonium bromide), DOTAP (dioleoyl-3-trimethylammonium-propane), and the like. Nonionic surfactants that have been proposed include, but are not limited to, PVA, povidone (also known as polyvinylpyrrolidone or PVP), sorbitan esters, polysorbates, polyoxyethylated glycol monoethers, polyoxyethylated alkyl phenols, poloxamers, and the like.

As used herein, a composition is "free of surfactant" or there is an "absence of surfactant" within a composition where the composition contains only insignificant or impurity amounts of a surfactant. As used herein an "insignificant" amount of surfactant means that the composition contains a weight-to-weight surfactant-to-polymer ratio of less than 0.00001:1.

The term "macromolecule" as used herein refers to, without limitation, a pharmaceutical, a polynucleotide, a polypeptide, a polypeptide-containing molecule, a hormone, an enzyme, a transcription or translation mediator, an intermediate in a metabolic pathway, an immunomodulator, an antigen, an adjuvant, or combinations thereof.

The term "pharmaceutical" refers to biologically active compounds such as antibiotics, antiviral agents, growth factors, hormones, and the like, discussed in more detail below.

The term "adjuvant" refers to any substance that assists or modifies the action of a pharmaceutical, including but not limited to immunological adjuvants, which increase or diversify the immune response to an antigen.

A "polynucleotide" is a nucleic acid polymer, which typically encodes a biologically active (e.g., immunogenic or therapeutic) protein or polypeptide. Depending on the nature of the polypeptide encoded by the polynucleotide, a polynucleotide can include as little as 10 nucleotides, e.g., where the polynucleotide encodes an antigen. Furthermore, a "polynucleotide" can include both double- and single-stranded sequences and refers to, but is not limited to, cDNA from viral, prokaryotic or eukaryotic mRNA, genomic RNA and DNA sequences from viral (e.g. RNA and DNA viruses and retroviruses) or prokaryotic DNA, and especially synthetic DNA sequences. The term also captures sequences that include any of the known base analogs of DNA and RNA. The term further includes modifications, such as deletions, additions and substitutions (generally conservative in nature), to a native sequence, preferably such that the nucleic acid molecule encodes a therapeutic or antigenic protein. These modifications may be deliberate, as through site-directed mutagenesis, or may be accidental, such as through mutations of hosts which produce the antigens.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature), to a native sequence, preferably such that the protein maintains the ability to elicit an immunological response or have a therapeutic effect on a subject to which the protein is administered.

By "antigen" is meant a molecule that contains one or more epitopes capable of stimulating a host's immune system to make a cellular antigen-specific immune response when the antigen is presented in accordance with the present invention, or a humoral antibody response. An antigen may be capable of eliciting a cellular or humoral response by itself or when present in combination with another molecule. Normally, an epitope will include between about 3-15, generally about 5-15, amino acids. Epitopes of a given protein can be identified using any number of epitope mapping techniques, well known in the art. See, e.g., *Epitope Mapping Protocols* in Methods in Molecular Biology, Vol.66 (Glenn E. Morris, Ed., 1996) Humana Press, Totowa, N.J. For example, linear epitopes may be determined by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra.

The term "antigen" as used herein denotes both subunit antigens, i.e., antigens which are separate and discrete from a whole organism with which the antigen is associated in nature, as well as killed, attenuated or inactivated bacteria, viruses, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses a therapeutic or immunogenic protein, or antigenic determinant in vivo, such as in gene therapy and nucleic acid immunization applications, is also included in the definition of antigen herein.

Further, for purposes of the present invention, antigens can be derived from any of several known viruses, bacteria, parasites and fungi, as well as any of the various tumor antigens. Furthermore, for purposes of the present invention, an "antigen" refers to a protein which includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts that produce the antigens.

An "immunological response" to an antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition, such as an immunogenic composition, or vaccine that elicits a cellular immune response, may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al., *J. Immunol.* (1993) 151:4189-4199; Doe et al., *Eur. J. Immunol* (1994) 24:2369-2376.

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

A composition which contains a selected antigen adsorbed to a microparticle, displays "enhanced immunogenicity" when it possesses a greater capacity to elicit an immune response than the immune response elicited by an equivalent amount of the antigen when delivered without association with the microparticle. Thus, a composition may display "enhanced immunogenicity" because the antigen is more strongly immunogenic by virtue of adsorption to the microparticle, or because a lower dose of antigen is necessary to achieve an immune response in the subject to which it is administered. Such enhanced immunogenicity can be determined by administering the microparticle/antigen composition, and antigen controls to animals and comparing, for example, antibody titers against the two using standard assays such as radioimmunoassay and ELISAs, well known in the art.

The terms "effective amount," "therapeutically effective amount" or "pharmaceutically effective amount" of a composition as provided herein, refer to a sufficient amount of the composition to treat or diagnose a condition of interest. For example, these expressions may refer to an amount sufficient to provide a desired response, such as an immunological response, and a corresponding prophylactic or therapeutic effect, or in the case of delivery of a therapeutic protein, an amount sufficient to effect treatment of the subject, as defined below. As will be pointed out below, the exact amount required will vary from subject to subject, depending on the species, age, and general condition of the subject, the severity of the condition being treated, the particular polypeptide of interest, mode of administration, and the like. An appropriate "effective" amount in any individual case may be determined by one of ordinary skill in the art using routine experimentation.

By "vertebrate subject" is meant any member of the subphylum cordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds. The term does not denote a particular age. Thus, both adult and newborn animals are intended to be covered.

By "pharmaceutically acceptable" or "pharmacologically acceptable" is meant a material which is not biologically or otherwise undesirable. For example, a "pharmaceutically acceptable" material may be administered to an individual along with the microparticle formulation without causing any undesirable biological effects in the individual or interacting in a deleterious manner with any of the components of the composition in which it is contained.

The term "excipient" refers to substances that are commonly provided within finished dosage forms, and include vehicles, binders, disintegrants, fillers (diluents), lubricants, glidants (flow enhancers), compression aids, colors, sweeteners, preservatives, suspending/dispersing agents, film formers/coatings, flavors and printing inks.

By "physiological pH" or a "pH in the physiological range" is meant a pH in the range of approximately 7.2 to 8.0 inclusive, more typically in the range of approximately 7.2 to 7.6 inclusive.

As used herein, "treatment" (including variations thereof, for example, "treat" or "treated") refers to any of (i) the prevention of infection or reinfection, as in a traditional vaccine, (ii) the reduction or elimination of symptoms, and (iii) the substantial or complete elimination of the pathogen or disorder in question. Treatment may be effected prophylactically (prior to infection) or therapeutically (following infection).

As used herein, the phrase "nucleic acid" refers to DNA, RNA, or chimeras formed therefrom.

As used herein, the phrase "oligonucleotide comprising at least one CpG motif" refers to a polynucleotide comprising at least one CpG dinucleotide. Oligonucleotides comprising at least one CpG motif can comprise multiple CpG motifs. These oligonucleotides are also known as "CpG oligonucleotides" in the art. As used herein, the phrase "CpG motif" refers to a dinucleotide portion of an oligonucleotide which comprises a cytosine nucleotide followed by a guanosine nucleotide. 5-methylcytosine can also be used in place of cytosine.

According to some embodiments of the present invention, compositions and methods are provided which treat, including prophylactically and/or therapeutically immunize, a host animal against viral, fungal, mycoplasma, bacterial, or protozoan infections, as well as to tumors. The methods of the present invention are useful for conferring prophylactic and/or therapeutic immunity to a mammal, preferably a human. The methods of the present invention can also be practiced on mammals other than humans, including biomedical research applications.

B. General Methods

Surprisingly, the present inventors have found that microparticles can be formed, and excellent adsorption of polypeptide-containing molecules to the microparticles can be achieved, without the use of surfactants. As a result, the microparticle/polypeptide-containing-molecule compositions of the present invention can be used as a delivery system to deliver biologically active polypeptide-containing molecules to a subject in order to prophylactically or therapeutically treat and/or diagnose a wide variety of diseases. While not wishing to be bound by theory, it is believed that the polymer materials used in connection with the present invention (e.g., PLG) typically have negatively charged groups, which give the microparticles of the present invention a net negative charge. This net negative charge leads to inter-microparticle repulsion, stabilizing the microparticles upon their formation. Moreover, this charge also attracts positively charged regions of the polypeptide-containing molecules, improving the adsorption of the polypeptide-containing molecules to the microparticles.

Many exemplary embodiments within the present patent application are directed to compositions containing microparticles with adsorbed polypeptide-containing molecules.

The present invention can be used in connection with the delivery of a wide variety of macromolecules including, but not limited to, pharmaceuticals such as antibiotics and antiviral agents, nonsteroidal antiinflammatory drugs, analgesics, vasodilators, cardiovascular drugs, psychotropics, neuroleptics, antidepressants, antiparkinson drugs, beta blockers, calcium channel blockers, bradykinin inhibitors, ACE-inhibitors, vasodilators, prolactin inhibitors, steroids, hormone antagonists, antihistamines, serotonin antagonists, heparin, chemotherapeutic agents, antineoplastics and growth factors, including but not limited to PDGF, EGF, KGF, IGF-1 and IGF-2, FGF, polynucleotides which encode therapeutic or immunogenic proteins, immunogenic proteins and epitopes thereof for use in vaccines, hormones including peptide hormones such as insulin, proinsulin, growth hormone, GHRH, LHRH, EGF, somatostatin, SNX-111, BNP, insulinotropin, ANP, FSH, LH, PSH and hCG, gonadal steroid hormones (androgens, estrogens and progesterone), thyroid-stimulating hormone, inhibin, cholecystokinin, ACTH, CRF, dynorphins, endorphins, endothelin, fibronectin fragments, galanin, gastrin, insulinotropin, glucagon, GTP-binding protein fragments, guanylin, the leukokinins, magainin, mastoparans, dermaseptin, systemin, neuromedins, neurotensin, pancreastatin, pancreatic polypeptide, substance P, secretin, thymosin, and the like, enzymes, transcription or translation mediators, intermediates in metabolic pathways, immunomodulators, such as any of the various cytokines including interleukin-1, interleukin-2, interleukin-3, interleukin-4, and gamma-interferon, antigens, and adjuvants.

The present invention is particularly well suited for the delivery of polypeptide-containing molecules to a subject. In some particularly preferred embodiments, the polypeptide-containing molecules are polypeptide antigen molecules. One advantage of microparticles with adsorbed polypeptide antigen molecules is their demonstrated ability to generate cell-mediated immune responses in a vertebrate subject. Thus, in addition to a conventional antibody response, the system herein described can provide for, e.g., the association of the expressed antigens with class I MHC molecules such that an in vivo cellular immune response to the antigen of interest can be mounted which stimulates the production of CTLs to allow for future recognition of the antigen. Furthermore, the methods may elicit an antigen-specific response by helper T-cells. Accordingly, the methods of the present invention will find use with any polypeptide-containing molecule for which cellular and/or humoral immune responses are desired, preferably antigens derived from viral and bacterial pathogens that may induce antibodies, T-cell helper epitopes and T-cell cytotoxic epitopes. Such antigens include, but are not limited to, those encoded by human and animal viruses and can correspond to either structural or non-structural proteins.

Hence, the ability of the antigen/microparticles of the invention to elicit a cell-mediated immune response against a selected antigen provides a powerful tool against infection by a wide variety of pathogens. Accordingly, the antigen/microparticle compositions of the present invention can be incorporated into vaccine compositions.

The microparticles of the present invention are particularly useful for immunuization against intracellular viruses which normally elicit poor immune responses. For example, the present invention will find use for stimulating an immune response against a wide variety of polypeptides from the herpes virus family, including proteins derived from herpes simplex virus (HSV) types 1 and 2, such as HSV-1 and HSV-2 glycoproteins gB, gD and gH; antigens derived from varicella zoster virus (VZV), Epstein-Barr virus (EBV) and cytomegalovirus (CMV) including CMV gB and gH; and antigens derived from other human herpes viruses such as HHV6 and HHV7. (See, e.g. Chee et al., *Cytomegaloviruses* (J. K. McDougall, ed., Springer-Verlag 1990) pp. 125-169, for a review of the protein coding content of cytomegalovirus; McGeoch et al., *J. Gen. Virol.* (1988) 69:1531-1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207-211, for the identification of protein coding sequences in an EBV genome; and Davison and Scott, *J Gen. Virol.* (1986) 67:1759-1816, for a review of VZV.)

Antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 (also known as E) and E2 (also known as E2/NS1) and an N-terminal nucleocapsid protein (termed "core") (see, Houghton et al., *Hepatology* (1991) 14:381-388, for a discussion of HCV proteins, including E1 and E2). Each of these proteins, as well as antigenic fragments thereof, will find use in the present composition and methods.

Similarly, the sequence for the δ-antigen from HDV is known (see, e.g., U.S. Pat. No. 5,378,814) and this antigen can also be conveniently used in the present composition and methods. Additionally, antigens derived from HBV, such as the core antigen, the surface antigen, sAg, as well as the presurface sequences, pre-S1 and pre-S2 (formerly called pre-S), as well as combinations of the above, such as sAg/pre-S1, sAg/pre-S2, sAg/pre-S1/pre-S2, and pre-S1/pre-S2, will find use herein. See, e.g., "HBV Vaccines—from the laboratory to license: a case study" in Mackett, M. and Williamson, J. D., *Human Vaccines and Vaccination*, pp. 159-176, for a discussion of HBV structure; and U.S. Pat. Nos. 4,722,840, 5,098,704, 5,324,513, incorporated herein by reference in their entireties; Beames et al., *J. Virol.* (1995) 69:6833-6838, Birnbaum et al., *J. Virol.* (1990) 64:3319-3330; and Zhou et al., *J. Virol.* (1991) 65:5457-5464.

Antigens derived from other viruses will also find use in the compositions and methods of the present invention, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Bimaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-I (also known as HTLV-II, LAV, ARV, hTLR, etc.)), including but not limited to antigens from the isolates $HIV_{IIIb}$, $HIV_{SF2}$, $HIV_{LAV}$, $HIV_{LA1}$, $HIV_{MN}$); $HIV-1_{CM235}$, $HIV-1_{US4}$; HIV-2; simian immunodeficiency virus (SIV) among others. Additionally, antigens may also be derived from human papillomavirus (HPV) and the tick-borne encephalitis viruses. See, e.g. Virology, 3rd Edition (W.

K. Joklik ed. 1988); *Fundamental Virology,* 2nd Edition (B. N. Fields and D. M. Knipe, eds. 1991), for a description of these and other viruses.

More particularly, the gp 120 or gp 140 envelope proteins from any of the above HIV isolates, including members of the various genetic subtypes of HIV, are known and reported (see, e.g., Myers et al., Los Alamos Database, Los Alamos National Laboratory, Los Alamos, N. Mex. (1992); Myers et al., *Human Retroviruses and Aids,* 1990, Los Alamos, N. Mex.: Los Alamos National Laboratory; and Modrow et al., *J Virol.* (1987) 61:570-578, for a comparison of the envelope sequences of a variety of HIV isolates) and antigens derived from any of these isolates will find use in the present methods. Furthermore, the invention is equally applicable to other immunogenic proteins derived from any of the various IIV isolates, including any of the various envelope proteins such as gp160 and gp41, gag antigens such as p24gag and p55gag, as well as proteins derived from the pol and tat regions.

Influenza virus is another example of a virus for which the present invention will be particularly useful. Specifically, the envelope glycoproteins HA and NA of influenza A are of particular interest for generating an immune response. Numerous HA subtypes of influenza A have been identified (Kawaoka et al., *Virology* (1990) 179:759-767; Webster et al., "Antigenic variation among type A influenza viruses," p. 127-168. In: P. Palese and D. W. Kingsbury (ed.), *Genetics of influenza viruses.* Springer-Verlag, New York). Thus, proteins derived from any of these isolates can also be used in the compositions and methods described herein.

The compositions and methods described herein will also find use with numerous bacterial antigens, such as those derived from organisms that cause diphtheria, cholera, tuberculosis, tetanus, pertussis, meningitis, and other pathogenic states, including, without limitation, *Bordetella pertussis, Neisseria meningitides* (A, B, C, Y), *Neisseria gonorrhoeae, Helicobacter pylori,* and *Haemophilus influenza. Hemophilus influenza* type B (HIB), *Helicobacter pylori,* and combinations thereof. Examples of antigens from *Neisseria meningitides* B are disclosed in the following co-owned patent applications: PCT/US99/09346; PCT IB98/01665; and PCT IB99/00103. Examples of parasitic antigens include those derived from organisms causing malaria and Lyme disease.

Additional antigens, which are not necessarily exclusive of those listed elsewhere in this application, include the following:

A protein antigen from *N. meningitidis* serogroup B, such as those in Refs. 1 to 7 below.

an outer-membrane vesicle (OMV) preparation from *N. meningitidis* serogroup B, such as those disclosed in Refs. 8, 9, 10, 11 etc. below.

a saccharide antigen from *N. meningitidis* serogroup A, C, W135 and/or Y, such as the oligosaccharide disclosed in Ref. 12 below from serogroup C (see also Ref. 13).

a saccharide antigen from *Streptococcus pneumnoniae* (e.g. Refs. 14, 15, 16).

an antigen from *N. gonorrhoeae* (e.g., Refs. 1, 2, 3).

an antigen from *Chlamydia pneumoniae* (e.g., Refs. 17, 18, 19, 20, 21, 22, 23).

an antigen from *Chlamydia trachomatis* (e.g. Ref. 24).

an antigen from hepatitis A virus, such as inactivated virus (e.g., Refs. 25, 26).

an antigen from hepatitis B virus, such as the surface and/or core antigens (e.g., Refs. 26, 27).

an antigen from hepatitis C virus (e.g. Ref. 28).

an antigen from *Bordetella pertussis,* such as pertussis holotoxin (PT) and filamentous haemaglutinin (FHA) from *B. pertussis,* optionally also in combination with pertactin and/or agglutinogens 2 and 3 (e.g., Refs. 29 & 30).

a diphtheria antigen, such as diphtheria toxoid (e.g., chapter 3 of Ref. 31) e.g. the $CRM_{197}$ mutant (e.g., Ref. 32).

a tetanus antigen, such as a tetanus toxoid (e.g., chapter 4 of Ref. 31).

a protein antigen from *Helicobacter pylori* such as CagA (e.g. Ref. 33), VacA (e.g. Ref. 33), NAP (e.g. Ref. 34), HopX (e.g. Ref. 35), HopY (e.g. Ref. 35) and/or urease.

a saccharide antigen from *Haemophilus influenzae* B (e.g. Ref. 13).

an antigen from *Porphyramonas gingivalis* (e.g. Ref. 36).

polio antigen(s) (e.g. Refs. 37, 38) such as IPV or OPV.

rabies antigen(s) (e.g. Ref. 39) such as lyophilized inactivated virus (e.g. Ref. 40, Rabavert™).

measles, mumps and/or rubella antigens (e.g., chapters 9, 10 and 11 of Ref. 31).

influenza antigen(s) (e.g. chapter 19 of Ref. 31), such as the haemagglutinin and/or neuraminidase surface proteins.

an antigen from *Moraxella catarrhalis* (e.g., Ref. 41).

an antigen from *Streptococcus agalactiae* (Group B streptococcus) (e.g. Refs. 42, 43)

an antigen from *Streptococcus pyogenes* (Group A streptococcus) (e.g. Refs. 43, 44, 45).

an antigen from *Staphylococcus aureus* (e.g. Ref. 46).

compositions comprising one or more of these antigens.

Where a saccharide or carbohydrate antigen is used, it is preferably conjugated to a carrier protein in order to enhance immunogenicity (e.g. Refs. 47 to 56). Preferred carrier proteins are bacterial toxins or toxoids, such as diphtheria or tetanus toxoids. The $CRM_{197}$ diphtheria toxoid is particularly preferred. Other suitable carrier proteins include *N. meningitidis* outer membrane protein (e.g. Ref. 57), synthetic peptides (e.g. Refs. 58, 59), heat shock proteins (e.g. Ref. 60), pertussis proteins (e.g. Refs. 61, 62), protein D from *H. Influenzae (e.g. Ref.* 63), toxin A or B from *C. difficile* (e.g. Ref. 64), etc. Where a mixture comprises capsular saccharides from both serogroups A and C, it is preferred that the ratio (w/w) of MenA saccharide:MenC saccharide is greater than 1 (e.g. 2:1, 3:1, 4:1, 5:1, 10:1 or higher). Saccharides from different serogroups of *N. meningitidis* may be conjugated to the same or different carrier proteins.

Any suitable conjugation reaction can be used, with any suitable linker where necessary.

Toxic protein antigens may be detoxified where necessary (e.g. detoxification of pertussis toxin by chemical and/or means (Ref. 30).

See: International patent application 99/24578 (Ref. 1); International patent application WO99/36544 (Ref. 2); International patent application WO99/57280 (Ref. 3); International patent application WO00/22430 (Ref. 4); Tettelin et al., (2000) *Science* 287:1809-1815 (Ref. 5); International patent application WO96/29412 (Ref. 6); Pizza el al. (2000) *Science* 287:1816-1820 (Ref. 7); International patent application PCT/IB01/00166 (Ref. 8); Bjune et al. (1991) *Lancet* 338 (8775):1093-1096 (Ref. 9); Fukasawa et al. (1990) *Vaccine* 17:2951-2958 (Ref. 10); Rosenqvist et al. (1998) *Dev. Biol. Stand.* 92:323-333 (Ref. 11); Costantino et al. (1992) *Vaccine* 10:691-698 (Ref. 12); Costantino et al. (1999) *Vaccine* 17:1251-1263 (Ref. 13); Watson (2000) *Padiatr Infect Dis J* 19:331-332 (Ref. 14); Rubin (2000) *Pediatr Clin North Am* 47:269-285, v (Ref. 15); Jedrzejas (2001) *Microbiol Mol Biol Rev* 65:187-207 (Ref. 16); International patent application filed on Jul. 3rd, 2001 claiming priority from GB-0016363.4 (Ref. 17); Kalman et al. (1999) *Nature Genetics* 21 :385-389 (Ref. 18); Read et al. (2000) *Nucleic Acids Res* 28:1397-406

(Ref. 19); Shirai et al. (2000) *J. Infect. Dis.* 181(Suppl 3):S524-S527 (Ref. 20); International patent application WO99/27105 (Ref. 21); International patent application WO00/27994 (Ref. 22); International patent application WO00/37494 (Ref. 23); International patent application WO99/28475 (Ref. 24); Bell (2000) *Pediat-Infect Dis J* 19:1187-1188 (Ref. 25); Iwarson (1995) *APMIS* 103:321-326 (Ref 26); Gerlich et al. (1990) *Vaccine* 8 Suppl:S63-68 & 79-80 (Ref. 27); Hsu et al. (1999) *Clin Liver Dis* 3:901-915 (Ref. 28); Gustafssonetal. (1996) *N. Engl. J. Med.* 334:349-355 (Ref. 29); Rappuoli et al. (1991) *TIBTECH* 9:232-238 (Ref. 30); Vaccines (1988) eds. Plotkin & Mortimer. ISBN 0-7216-1946-0 (Ref. 31); Del Guidice et al. (1998) *Molecular Aspects of Medicine* 19:1-70 (Ref. 32); International patent application WO93/18150 (Ref. 33); International patent application WO99/53310 (Ref. 34); International patent application WO98/04702 (Ref. 35); Ross et al. (2001) *Vaccine* 19:4135-4142 (Ref. 36); Sutter et al. (2000) *Pediatr Clin North Am* 47:287-308 (Ref. 37); Zimmerman & Spann (1999) *Am Fam Physicial* 59:113-118, 125-126 (Ref. 38); Dreesen (1997) *Vaccine* 15 Suppl:S2-6 (Ref. 39); *MMWR Morb Mortal Wkly Rep* 1998 January 16;47(1):12, 19 (Ref. 40); McMichael (2000) *Vaccine* 19 Suppl 1:S 101-107 (Ref. 41); Schuchat (1999) *Lancet* 353(9146):51-6 (Ref. 42); GB patent applications 0026333.5, 0028727.6 & 0105640.7 (Ref. 43); Dale (1999) *Infect Dis Clin North Am* 13:22743, viii (Ref. 44); Ferretti et al. (2001) *PNAS USA* 98:4658-4663 (Ref. 45); Kuroda et al. (2001) *Lancet* 357(9264):1225-1240; see also pages 1218-1219 (Ref. 46); Ramsay et al. (2001) *Lancet* 357(9251):195-196 (Ref 47); Lindberg (1999) *Vaccine* 17 Suppl 2:S28-36 (Ref. 48); Buttery & Moxon (2000) *J R Coll Physicians London* 34:163-168 (Ref. 49); Ahmad & Chapnick (1999) *Infect Dis Clin North Am* 13:113-133, vii (Ref. 50); Goldblatt (1998) *J. Med. Microbiol.* 47:563-567 (Ref. 51); European patent 0 477 508 (Ref. 52); U.S. Pat. No. 5,306,492 (Ref. 53); International patent application WO98/42721 (Ref. 54); *Conjugate Vaccines* (eds. Cruse et al.) ISBN 3805549326, particularly vol. 10:48-114 (Ref. 55); Hermanson (1996) *Bioconjugate Techniques* ISBN: 0123423368 & 012342335X (Ref. 56); European patent application 0372501 (Ref. 57); European patent application 0378881 (Ref 58); European patent application 0427347 (Ref. 59); International patent application WO93/17712 (Ref. 60); International patent application WO98/58668 (Ref. 61); European patent application 0471177 (Ref. 62); International patent application WO00/56360 (Ref. 63); international patent application WO00/61761 (Ref. 64).

Where diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

It is readily apparent that the present invention can be used to deliver a wide variety of polypeptide-containing molecules and hence to treat and/or diagnose a large number of diseases. In some embodiments, the polypeptide-containing-molecule/microparticle compositions of the present invention can be used for site-specific targeted delivery. For example, intravenous administration of the polypeptide-containing-molecule/microparticle compositions can be used for targeting the lung, liver, spleen, blood circulation, or bone marrow.

The adsorption of polypeptide-containing molecules to the surface of the adsorbent microparticles occurs via any bonding-interaction mechanism, including, but not limited to, ionic bonding, hydrogen bonding, covalent bonding, Van der Waals bonding, and bonding through hydrophilic/hydrophobic interactions.

Biodegradable polymers for manufacturing microparticles for use with the present invention are readily commercially available from, e.g., Boehringer Ingelheim, Germany and Birmingham Polymers, Inc., Birmingham, Ala. For example, useful polymers for forming the microparticles herein include homopolymers, copolymers and polymer blends derived from the following: polyhydroxybutyric acid (also known as polyhydroxybutyrate); polyhydroxy valeric acid (also known as polyhydroxyvalerate); polyglycolic acid (PGA) (also known as polyglycolide): polylactic acid (PLA) (also known as polylactide); polydioxanone; polycaprolactone; polyorthoester; and polyanhydride. More preferred are poly($\alpha$-hydroxy acid), such as poly(L-lactide), poly(D,L-lactide) (both known as "PLA" herein), poly(hydoxybutyrate), copolymers of D,L-lactide and glycolide, such as poly(D,L-lactide-co-glycolide) (designated as "PLG" herein) or a copolymer of D,L-lactide and caprolactone. Particularly preferred polymers for use herein are PLA and PLG polymers. These polymers are available in a variety of molecular weights, and the appropriate molecular weight for a given use is readily determined by one of skill in the art. Thus, e.g., for PLA, a suitable molecular weight will be on the order of about 2000 to 5000. For PLG, suitable molecular weights will generally range from about 10,000 to about 200,000, preferably about 15,000 to about 150,000.

If a copolymer such as PLG is used to form the microparticles, a variety of lactide:glycolide molar ratios will find use herein and the ratio is largely a matter of choice, depending in part on the coadministered polypeptide-containing molecule and the rate of degradation desired. For example, a 50:50 PLG polymer, containing 50% D,L-lactide and 50% glycolide, will provide a fast resorbing copolymer while 75:25 PLG degrades more slowly, and 85:15 and 90:10, even more slowly, due to the increased lactide component. It is readily apparent that a suitable ratio of lactide:glycolide is easily determined by one of skill in the art based, for example, on the nature of the antigen and disorder in question. Degradation rate of the microparticles of the present invention can also be controlled by such factors as polymer molecular weight and polymer crystallinity. PLG copolymers with varying lactide:glycolide ratios and molecular weights are readily available commercially from a number of sources including from Boehringer Ingelheim, Germany and Birmingham Polymers, Inc., Birmingham, Ala. Some exemplarly PLG copolymers include: (a) RG 502, a PLG having a 50:50 lactide/glycolide molar ratio and a molecular weight of 12,000 Da; (b) RG 503, a PLG having a 50:50 lactide/glycolide molar ratio and a molecular weight of 34,000 Da; (c) RG 504, a PLG having a 50:50 lactide/glycolide molar ratio and a molecular weight of 48,000 Da, (d) RG 752, a PLG having a 75:25 lactide/glycolide molar ratio and a molecular weight of 22,000 Da; and (e) RG 755, a PLG having a 75:25 lactide/glycolide molar ratio and a molecular weight of 68,000 Da. PLG polymers can also be synthesized by simple polycondensation of the lactic acid component using techniques well known in the art, such as described in Tabata et al., *J. Biomed. Abater. Res.* (1988) 22:837-858. Presently preferred PLG copolymers are those having a molar lactide/glycolide ratio ranging from 25:75 to 75:25, more preferably 40:60 to 60:40, and having a molecular weight ranging from 10,000 to 100,000 Daltons, more preferably from 20,000 Daltons to 70,000 Daltons.

The microparticles are prepared using any of several methods well known in the art. For example, in some embodiments, double emulsion/solvent evaporation techniques, such as those described in U.S. Pat. No. 3,523,907 and Ogawa et al., *Chem Pharm. Bull.* (1988) 36:1095-1103, can be used herein to make the microparticles. These techniques involve the formation of a primary emulsion consisting of droplets of polymer solution, which is subsequently mixed with a continuous aqueous phase containing a particle stabilizer/surfactant.

In other embodiments, microparticles can also be formed using spray-drying and coacervation as described in, e.g., Thomasin et al., *J. Controlled Release* (1996) 41:131; U.S. Pat. No. 2,800,457; Masters, K. (1976) *Spray Drying* 2nd Ed. Wiley, New York; air-suspension coating techniques, such as pan coating and Wurster coating, as described by Hall et al., (1980) The "Wurster Process" in *Controlled Release Technologies. Methods, Theory, and Applications* (A. F. Kydonieus, ed.), Vol. 2, pp. 133-154 CRC Press, Boca Raton, Fla. and Deasy, P. B., *Crit. Rev. Ther. Drug Carrier Syst.* (1988) S(2):99-139; and ionic gelation as described by, e.g., Lim et al., *Science* (1980) 210:908-910.

In preferred embodiments, a modified water-in-oil-in-water (w/o/w) solvent evaporation technique can be used to form the microparticles. Techniques of this type have been described, for example, in O'Hagan et al., *Vaccine* (1993) 11:965-969, PCT/US99/17308 (WO 00/06123) to O'Hagan et al., and Jeffery et al., Pharm. Res. (1993) 10:362. These techniques, however, are modified for use in connection with the present invention. Specifically, distinct from these techniques, the w/o/w emulsions of the present invention are preferably formed in the absence of surfactants (including detergents, dispersing agents, suspending agents and emulsion stabilizers).

More specifically, a particular polymer of interest such as PLG, is dissolved in an organic solvent, such as ethyl acetate, dimethyl chloride (also called methylene chloride and dichloromethane), acetonitrile, acetone, chloroform, and the like. The polymer will typically be provided in about a 1-30%, preferably about a 2-15%, more preferably about a 3-10% and most preferably, about a 4-6% solution, in organic solvent. The polymer solution is then combined with a first volume of an aqueous solution and emulsified to form an o/w emulsion. The aqueous solution can be, for example, deionized water, normal saline, or a buffered solution such as phosphate-buffered saline (PBS) or a sodium citrate/ethylenediaminetetraacetic acid (sodium citrate/ETDA) buffer solution. The latter solutions can (a) provide a tonicity, i.e., osmolality, that is essentially the same as normal physiological fluids and (b) maintain a pH compatible with normal physiological conditions. Alternatively, the tonicity and/or pH characteristics of the compositions of the present invention can be adjusted after microparticle formation and prior to administration.

Preferably, the volume ratio of polymer solution to aqueous solution ranges from about 5:1 to about 20:1, and is more preferably about 10:1. Emulsification is preferably conducted using any equipment appropriate for this task, and is typically a high-shear device such as, e.g., an homogenizer.

A volume of the o/w emulsion is then preferably combined with a larger second volume of aqueous solution, which can also be, for example, deionized water, normal saline, or a buffered solution. The ratio of the second volume of aqueous solution to the volume of the o/w emulsion typically ranges from about 2:1 to 10:1, and is more typically about 4:1. The mixture is then homogenized to produce a w/o/w double emulsion. Organic solvents are then evaporated.

The formulation parameters can be manipulated to allow the preparation of small microparticles on the order of 0.2 µm (200 nm) to larger microparticles 50 µm or even larger. See, e.g., Jeffery et al., *Pharm. Res.* (1993) 10:362-368; McGee et al., *J. Microencap.* (1996). For example, reduced agitation results in larger microparticles, as does an increase in internal phase volume and an increase in polymer concentration. Small particles are produced by increased agitation as well as low aqueous phase volumes and low polymer concentration.

One preferred apparatus for performing the above steps is schematically illustrated in FIG. 1. Referring now to FIG. 1, a manufacturing tank assembly, generally designated by the numeral 102, is shown. The tank assembly 102 is designed to be a "closed system," such that an aseptic environment is maintained during processing. All pieces of equipment and parts are preferably selected to be clean-in-place and autoclavable. All filters 104a-d are preferably fluoropolymer filters such as Super-Cheminert™ all-fluoropolymer filters from Pall Corporation. Initially, an aqueous solution, such as a deionized water 106 and an organic polymer solution, such as a solution of PLG in methylene chloride 108, are filtered and fed into tank 110 where they are continuously mixed with mixer 112. The mixture is then fed through an in-line homogenizer 114 (e.g., a high speed, high shear autoclavable in-line homogenizer such as the Kinematica MT 5000), forming an o/w emulsion. The emulsion is cooled, for example by a water-cooled condenser 116, after emerging from the in-line homogenizer 114, whereupon it is returned to the tank 110. After the contents are emulsified to the desired extent, additional aqueous solution, such as deionized water 106, is added to the tank 110, whereupon a w/o/w emulsion is formed by again feeding the contents through the in-line mixer 114. The resulting w/o/w emulsion is purged with nitrogen via distributor 119 to remove the organic solvent. The nitrogen-laden solvent vapor is filtered and cooled in a condenser 120, capturing the solvent in container 122. Where the emulsion is somewhat unstable, it may be desirable to remove the solvent concurrently with in-line mixing.

Particle size can be determined by, e.g., laser light scattering, using for example, a spectrometer incorporating a helium-neon laser. Generally, particle size is determined at room temperature and involves multiple analyses of the sample in question (e.g., 5-10 times) to yield an average value for the particle diameter. Particle size is also readily determined using scanning electron microscopy (SEM).

Following preparation, microparticles can be stored as is or lyophilized for future use. In order to adsorb polypeptide-containing molecules to the microparticles, the microparticle preparation can be simply mixed with the polypeptide-containing molecule of interest and the resulting formulation can again be lyophilized prior to use.

Typically, polypeptide-containing molecules are added to the microparticles to yield microparticles with adsorbed polypeptide-containing molecules having a polypeptide-containing molecule to microparticle weight-to-weight ratio of from about 0.0001:1 to 0.25:1, more typically 0.001:1 to 0.1:1, even more typically 0.05:1 to 0.01:1. The polypeptide-containing-molecule content of the microparticles can be determined using standard techniques.

In addition to microparticles with adsorbed polypeptide-containing molecules, the compositions of the present invention can also include a variety of other macromolecules (including additional polypeptide-containing molecules, pharmaceuticals, polynucleotides, hormones, enzymes, transcription or translation mediators, metabolic pathway intermediates, immunomodulators, antigens, adjuvants or combinations thereof.) For example, the microparticles of the present invention may have additional macromolecules entrapped or encapsulated within them, adsorbed on their surfaces, or included in solution or in suspension. Particularly preferred additional macromolecules are adjuvants.

Once the microparticles with adsorbed polypeptide-containing molecules are produced, they are formulated into pharmaceutical compositions, including vaccines, to treat and/or diagnose a wide variety of disorders, as described above. The compositions will generally include one or more pharmaceutically acceptable excipients. For example, vehicles such as water, saline, glycerol, polyethylene glycol, hyaluronic acid, ethanol, etc. may be used. Other excipients, such as wetting or emulsifying agents, biological buffering substances, and the like, may be present in such vehicles. A biological buffer can be virtually any substance which is pharmacologically acceptable and which provides the formulation with the desired pH, i.e., a pH in the physiological range. Examples of buffer solutions include phosphate buffered saline (PBS), Tris buffered saline, Hank's buffered saline, and the like. Other excipients known in the art can also be introduced into the final dosage form, including binders, disintegrants, fillers (diluents), lubricants, glidants (flow enhancers), compression aids, colors, sweeteners, preservatives, suspending/dispersing agents, film formers/coatings, flavors and printing inks.

Adjuvants may be used to enhance the effectiveness of the pharmaceutical compositions. The adjuvants may be administered concurrently with the microparticles of the present invention, e.g., in the same composition or in separate compositions. Alternatively, the adjuvant may be administered prior or subsequent to the microparticle compositions of the present invention. In some embodiments, the adjuvant, such as an immunological adjuvant, may be encapsulated in the microparticle. Adjuvants, just as any macromolecule, may be encapsulated within the microparticles using any of the several methods known in the art. See, e.g., U.S. Pat. No. 3,523,907; Ogawa et al., *Chem. Pharm. Bull.* (1988) 36:1095-1103; O'Hagan et al., *Vaccine* (1993) 11:965-969 and Jefferey et al., *Pharm. Res.* (1993) 10:362. Alternatively, some adjuvants, particularly polypeptide-containing adjuvants, may be adsorbed on the microparticle as described above.

Immunological adjuvants include, but are not limited to: (1) aluminum salts (alum), such as aluminum hydroxide, aluminum phosphate, aluminum sulfate, etc.; (2) other oil-in water emulsion formulations (with or without other specific immunostimulating agents such as muramyl peptides (see below) or bacterial cell wall components), such as for example (a) MF59 (International Publication No. WO90/14837; Chapter 10 in *Vaccine design: the subunit an adjuvant approach*, Eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™) (for a further discussion of suitable submicron oil-in-water emulsions for use herein, see commonly owned, patent application Ser. No. 09/015,736, filed on Jan. 29, 1998); (3) saponin adjuvants, such as Quil A, or QS21 (e.g., Stimulon™ (Cambridge Bioscience, Worcester, Mass.)) may be used or particles generated therefrom such as ISCOMs (immunostimulating complexes), which ICOMS may be devoid of additional detergent e.g., WO00/07621; (4) Complete Freunds Adjuvant (CFA) and Incomplete Freunds Adjuvant (IFA); (5) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (6) monophosphoryl lipid A (MPL) or 3-O-deacylated MPL (3dMPL) e.g. GB-2220221, EP-A-0689454, optionally in the substantial absence of alum when used with pneumococcal saccharides e.g. WO00/56358; (7) combinations of 3dMPL with, for example, QS21 and/or oil-in-water emulsions, e.g., EP-A-0835318, EP-A-0735898, EP-A-076123 1; (8) oligonucleotides comprising CpG motifs (Roman et al., *Nat. Med.*, 1997, 3, 849-854; Weiner et al., *PNAS USA*, 1997, 94, 10833-10837; Davis et al., *J Immunol.* 1988, 160, 870-876; Chu et al., *J. Exp. Med.*, 1997, 186, 1623-1631; Lipford et al., *Eur. J. Immunol.* 1997, 27, 2340-2344; Moldoveanu et al., *Vaccine*, 1988, 16, 1216-1224, Krieg et al., *Nature*, 1995, 374, 546-549; Klinman et al., *PNAS USA*, 1996, 93, 2879-2883: Ballas et al., *J. Immunol.*, 1996, 157, 1840-1845; Cowdery et al., *J. Immunol.*, 1996, 156, 45704575; Halpern et al., *Cell. Immunol.*, 1996, 167, 72-78; Yamamoto et al., *Jpn. J. Cancer Res.*, 1988, 79, 866-873; Stacey et al., *J. Immunol*, 1996, 157,2116-2122; Messina et al., *J. Immunol*, 1991, 147, 1759-1764; Yi et al., *J. Immunol.*, 1996, 157, 4918-4925; Yi et al., *J. Immunol.*, 1996, 157, 5394-5402; Yi et al., *J. Immunol.*, 1998, 160, 47554761; and Yi et al., *J. Immunol.*, 1998, 160, 5898-5906; International patent applications WO96/02555, WO98/16247, WO98/18810, WO98/40100, WO98/55495, WO98/37919 and WO98/52581) i.e. containing at least one CG dinucleotide, with 5 methylcytosine optionally being used in place of cytosine; (9) a polyoxyethylene ether or a polyoxyethylene ester e.g. WO99/52549; (10) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (11) a saponin and an immunostimulatory oligonucleotide (e.g., a CpG oligonucleotide) (WO00/62800); (12) an immunostimulant and a particle of metal salt e.g. WO00/23105; (13) a saponin and an oil-in-water emulsion e.g. WO99/11241; (14) a saponin (e.g. QS21)+3dMPL+IL-12 (optionally+a sterol) e.g. WO98/57659; (15) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S 109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); (16) aminoalkyl glucosaminide 4-phosphates (AGP's), see, e.g., Johnson, D. A. et al.; Bioorg. Med. Chem. Lett., 1999 Aug. 2; 9(15):2273-8, (17) imidazoquinolines such as imiquimod (R-837) and resiquimod (R-848), see, e.g., Vasilakos, J. P. et al.; Cell. Immunol. 2000 Aug. 25; 204(l):64-74, (18) lipopolysaccharide mimetics, including non-saccharide phospholipids (e.g., simplified lipid A analogs lacking a disaccharide) described in Hawkins, L. D. et al; J. Pharmacol. Exp. Ther., 2002 February; 300(2):655-61, and (19) other substances that act as immunostimulating agents to enhance the effectiveness of the composition.

Muramyl peptides include, but are not limited to, N-acetyl-muramyl-L-threonyl-D-isoglutamine (thr-MDP), N-acetyl-nomuramyl-L-alanyl-D-isogluatme (nor-MDP), N-acetylmuramyl-L-alanyl-D-isogluatminyl-L-alanine-2-(1'-2'-dipalmitoyl-sn-glycero-3-huydroxyphosphoryloxy)-ethylamine (MTP-PE), etc.

For additional examples of adjuvants, see *Vaccine Design:, The Subunit and the Adjuvant Approach*, Powell, M. F. and Newman, M. J, eds., Plenum Press, 1995)

The compositions will comprise a "therapeutically effective amount" of the polypeptide-containing molecule (as well as any other macromolecule) of interest. That is, a sufficient amount of the polypeptide-containing molecule will be included to treat or diagnose a condition of interest. The exact amount necessary will vary, for example, depending on the subject being treated; the age and general condition of the subject to be treated; the severity of the condition being treated; in the case of an immunological response, the capacity of the subject's immune system to synthesize antibodies; the degree of protection desired and the particular polypeptide-containing molecule selected and its mode of administration, among other factors. An appropriate effective amount can be readily determined by one of skill in the art. Thus, a "therapeutically effective amount" will typically fall in a relatively broad range that can be determined through routine trials. For example, where the macromolecule is a polypeptide antigen, an effective dose will typically range from about 1 µg to about 100 mg, preferably from about 5 µg to about 1 mg, more preferably about 5 µg to about 100 µg and most preferably about 5 µg to about 50 µg of the antigen delivered per dose.

Once formulated, the compositions of the invention can be administered parenterally, e.g., by injection. The compositions can be injected either subcutaneously, intraperitoneally, intravenously or intramuscularly. Other modes of administration include nasal, mucosal, rectal, vaginal, oral and pulmonary administration, suppositories, and transdermal or transcutaneous applications.

Dosage treatment may be a along a single dose schedule or a multiple dose schedule. A multiple dose schedule is one in which a primary course of administration may be with 1-10 separate doses, followed by other doses given at subsequent time intervals, chosen to maintain and/or reinforce the therapeutic response, for example at 1-4 months for a second dose, and if needed, a subsequent dose(s) after several months. The dosage regimen will also, at least in part, be determined by the need of the subject and be dependent on the judgment of the practitioner.

Furthermore, if prophylactic treatment is desired, for example, in vaccines, compositions of the present invention are generally administered prior to primary infection with the pathogen of interest. If therapeutic treatment is desired, e.g., the reduction of symptoms or recurrences, the compositions of the present invention are generally administered subsequent to primary infection.

C. Experimental

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

EXAMPLE 1

Preparation of PLG Particles with No Surfactant 2.5 ml PBS is homogenized with 10 ml 6% RG503 (a PLG Polymer having a 50:50 lactide/glycolide molar ratio and a molecular weight of 34,000 Daltons, available from Boehringer Ingelheim) in dimethyl chloride with a small probe of the IKA homogenizer (Germany) at 23,000 rpm for 2 minutes. This primary o/w emulsion is added to 50 ml of deionized water, followed by homogenization with a 10 mm probe of the Omni benchtop homogenizer (LabTek Inc, US) at 15,000 rpm for 30 minutes in an ice bath. The container is sealed using Teflon tape with the homogenizer inserted into the liquid to prevent solvent evaporation during homogenization. The Teflon tape is removed, and this secondary w/o/w emulsion is left stirring overnight to allow for solvent evaporation. The next day the particle size is measured using a Malvern Master Sizer. The size range is typically 0.5-1 micron.

EXAMPLE 2

Preparation of PLG Particles with 0.05% and 0.5% wt:wt DSS to PLG 2.5 ml PBS is homogenized with 10 ml 6% RG503 (a PLG Polymer having a 50:50 lactide/glycolide molar ratio and a molecular weight of 34,000 Daltons, available from Boehringer Ingelheim) in dimethyl chloride with a small probe of the IKA homogenizer (Germany) at 23,000 rpm for 2 minutes. This primary o/w emulsion is added to 50ml of deionized water, containing either 6 ug/ml or 60 ug/ml DSS for 0.05% and 0.5% respectively. This is followed by homogenization with a 10 mm probe of the Omni benchtop homogenizer (LabTek Inc, US) at 15,000 rpm for 30 minutes in an ice bath. The container is sealed using Teflon tape with the homogenizer inserted into the liquid to prevent solvent evaporation during homogenization. The Teflon tape is removed, and this secondary w/o/w emulsion is left stirring overnight to allow for solvent evaporation. The next day the particle size is measured using a Malvern Master Sizer. The size range is typically 0.5-1 micron.

EXAMPLE 3

Preparation of PLG Particles (Conventional Formulation)

2.5 ml PBS is homogenized with 10 ml 6% RG503 (a PLG Polymer having a 50:50 lactide/glycolide molar ratio and a molecular weight of 34,000 Daltons, available from Boehringer Ingelheim) in dimethyl chloride with a small probe of the IKA homogenizer (Germany) at 23,000 rpm for 2 minutes. This primary o/w emulsion is added to 50 ml of deionized water, containing 1% wt:vol DSS. This is followed by homogenization with a 10 mm probe of the Omni benchtop homogenizer (LabTek Inc, US) at 10,000 rpm for 3 minutes at room temperature. This secondary w/o/w emulsion is left stirring overnight to allow for solvent evaporation. The next day the particle size is measured using a Malvern Master Sizer. The size range is typically 0.5-1 micron.

EXAMPLE 4

Protein Adsorption to PLG Formulations

PLG particles made with 0%, 0.05% and 0.5% wt:wt DSS (from Examples 1 and 2 above) were adsorbed to meningitis B 287 protein, (Chiron protein purification group, Siena, Italy. Vol. 287 Science, 1816 (2000)) as follows: Direct binding to PLG particles with 0%, 0.05% and 0.5% DSS:

1—The suspension volume for each formulation in Examples 1 and 2, was measured and PLG content was estimated by dividing the starting weight of PLG by the total volume.
2—For each formulation, a specific volume containing 200 mg of PLG was placed in a 30 ml centrifuge tube and 2 mg of 287 protein were added.
3—The buffer was adjusted to 10 mM Citrate by adding 1 ml of 100 mM Citrate pH4.75 and the total volume was brought up to 10 ml with DI water.
4—The tube was left rocking on a lab rocker at 4° C. overnight.
5—The next day, a 2 ml aliquot was withdrawn for analysis and the remaining suspension was aliquot into vials, each containing 12 doses of either 1ug or 10 ug of protein on PLG per dose.
6—216 ul of 25% wt:vol solution of Mannitol in water were added to each vial prior to lyophilization.

EXAMPLE 5

Protein Adsorption to PLG/DSS Formulation made by the Conventional Method

1—The suspension in Example 3 was washed with 250 ml water by centrifugation twice.
2—The pellet is resuspended in 15 ml DI water and sonicated in a water bath sonicator for 2 minutes.
3-5 ml of the suspension (containing 200 mg PLG ) was placed in a 30 ml centrifuge tube and 2 mg 287 protein was added.
4—The buffer was adjusted by adding 1 ml 10×PBS and the volume brought up to 10 ml with DI water.
5—The suspension was allowed to rock on a lab rocker overnight at 4° C.
6—The next day a 1 ml aliquot was withdrawn for analysis and the remaining suspension was transferred to a 12-14M wt. Cut off dialysis tubing and dialyzed against 4 changes of 4 L DI water each.
7—The total volume was measured and a 1 ml aliquot was withdrawn for analysis. The remaining suspension was aliquoted into vials, each containing either 1 ug or 10 ug protein on PLG.
8—216 ul of a 25% solution of Mannitol in DI water was added to each vial before lyophilization.

EXAMPLE 6

Characterization

1—1 ml of each suspension (from Example 4, step 5) was dialyzed in a 12-14 M wt. Cut off dialysis tubing against 2 changes of 4 L water each, overnight, and lyophilized.
2—The remaining 1 ml of each suspension (from Example 4, step 5) and the aliquot from Example 5 step 6, were each washed with 30 ml water by centrifugation and lyophilized.
3—1 ml aliquot from Example 5, step 7 was lyophilized.
4—5 mg of each lyophilized formulation from steps 1, 2 and 3 above, were hydrolyzed with 1 ml each 0.2 NNaOH/5% SDS, and protein content measured by Micro BCA assay from Pierce, USA.
5—10 mg each of unwashed particles (from steps 1 and 3 above) were resuspended in 1 ml PBS and left rocking at 37° C. for one hour and burst release was determined by measuring protein in the supernatant by Micro BCA assay from Pierce, USA.

| Formulation | Washed Post-adsorption % load wt:wt | Unwashed Post-adsorption % load wt:wt | % 1 hour release | Size microns D50-90 |
|---|---|---|---|---|
| 0% DSS/287 | 0.63 | 1 | 65 | 0.82-1.2 |
| 0.05% DSS/287 | 0.85 | 1 | 56 | 0.9-1.5 |
| 0.5% DSS/287 | 0.61 | 1 | 29 | 3.8-9.3 |
| Conventional formulation/287 | 0.87 | 1 | 40 | 9-28 |

EXAMPLE 7

In Vivo Data

Groups of 10 CD 1 mice each, were immunized intramuscularly with 100 ul containing either 10 ug or 1 ug of protein adsorbed onto PLG particles from Example 4, step 5 and Example 5, step 7 at 0, 3 and 5 week intervals and sera was collected at weeks 5 and 7.

Enzyme-linked immunosorbent assay designed to measure MenB-specific antibody was performed on mice sera at week 5 and 7. Purified 287 protein was coated onto Nunc Maxisorp U bottom plates (Nalgene Nunc International) at 1 ug/ml. Sera were tested at 1:100 and 1:400 dilutions followed by serial three fold dilutions. Horseradish peroxidase-conjugated goat anti mouse IgG (CALTAG diluted 1:40,000) was used as a second antibody. After the one-hour incubation at 37° C., plates were washed to remove unbound antibody. TMB (Kirkegaard and Perry Laboratories, KPL) substrate was used to develop the plates and the color reaction was blocked after 15 minutes by addition of 2N HCl. The titers reported, geometric mean titer (GMT) along with standard error (STE), are the reciprocal of the serum dilutions that gave an optical density at 450 nm of 0.5 ELISA absorbency units.

| Formulation | Dose | 2 weeks post 2nd GMT | STE | 2 weeks post 3rd GMT | STE |
|---|---|---|---|---|---|
| 0% DSS/287 | 1 ug | 407 | 331 | 1,159 | 2,389 |
|  | 10 ug | 4,324 | 1,771 | 7,138 | 2,223 |
| 0.05% DSS/287 | 1 ug | 889 | 390 | 3,314 | 473 |
|  | 10 ug | 7,586 | 3,494 | 10,274 | 3,016 |
| 0.5% DSS/287 | 1 ug | 1,380 | 2,369 | 2,316 | 1,253 |
|  | 10 ug | 1,963 | 1,573 | 4,551 | 1,175 |
| Conventional formulations | 1 ug | 334 | 510 | 1,288 | 586 |
|  | 10 ug | 1,779 | 1,340 | 4,020 | 1,457 |

Although preferred embodiments of the subject invention have been described in some detail, it is understood that obvious variations can be made without departing from the spirit and the scope of the invention.

What is claimed is:

1. A microparticle composition comprising: (a) microparticles comprising a polymer selected from the group consisting of a poly(α-hydroxy acid), a polyhydroxy butyric acid, a polycaprolactone, a polyorthoester, a polyanhydride, and a polycyanoacrylate; and (b) a polypeptide-containing molecule adsorbed to the microparticles, wherein the microparticle composition is formed in the absence of surfactant and wherein the microparticles do not contain entrapped or encapsulated polypeptide-containing molecules.

2. The microparticle composition of claim 1, wherein the polymer comprises a poly(α-hydroxy acid).

3. The microparticle composition of claim 2, wherein the poly(α-hydroxy acid) is selected from the group consisting of poly(L-lactide), poly(D,L-lactide) and poly(D,L-lactide-co-glycolide).

4. The microparticle composition of claim 3, wherein the polymer comprises poly(D,L-lactide-co-glycolide).

5. The microparticle composition of claim 4, wherein the poly(D,L-lactide-co-glycolide) has a lactide/glycolide molar ratio ranging from 25:75 to 75:25 and a molecular weight ranging from 10,000 to 100,000 Daltons.

6. The microparticle composition of claim 4, wherein the poly(D,L-lactide-co-glycolide) has a lactide/glycolide molar ratio ranging from 40:60 to 60:40 and a molecular weight ranging from 20,000 Daltons to 70,000 Daltons.

7. The microparticle composition of any of claims 1-6, wherein the polypeptide-containing molecule is an antigen.

8. The microparticle composition of claim 7, wherein the antigen is selected from HIV antigens, meningitis B antigens, streptococcus antigens, hepatitis B virus antigens, hepatitis C virus antigens, *Haemophilis influenza* type B antigens, pertussis antigens, diphtheria antigens, tetanus antigens, *Helicobacter pylori* antigens and Influenza A hemagglutinin antigens.

9. The microparticle composition of claim 7, wherein the antigen is selected from the group consisting of HIV gp41 antigen, HIV gp120 antigen, HIV gp140 antigen, HIV p24gag antigen, HIV p55gag antigen, meningitis B recombinant protein 287 antigen, and group B streptococcus antigen.

10. The microparticle composition of claim 1, further comprising a pharmaceutically acceptable excipient.

11. The microparticle composition of claim 10, further comprising an additional biologically active macromolecule selected from the group consisting of a polynucleotide, a polynucleoside, a pharmaceutical, a hormone, an enzyme, a transcription or translation mediator, an intermediate in a metabolic pathway, an immunomodulator, and an adjuvant.

12. The microparticle composition of claim 11, wherein the additional biologically active macromolecule is an adjuvant.

13. The microparticle composition of claim 12, wherein the adjuvant is a member selected from the group consisting of CpG oligonucleotides, double-stranded RNA adjuvants, aminoalkyl glucosaminide 4-phosphate adjuvants, imidazoquinoline adjuvants, lipopolysaccharide mimetic adjuvants, saponin adjuvants, *E. coli* heat-labile toxin adjuvants, monophosphorylipid A adjuvants and aluminum salts.

14. The microparticle composition of claim 12, wherein the adjuvant is aluminum phosphate.

15. A method of delivering a therapeutically effective amount of a polypeptide-containing molecule to a vertebrate subject, the method comprising the step of administering to the vertebrate subject the microparticle composition of any of claims 10-14.

16. The microparticle composition of claim 7, wherein the antigen comprises a polysaccharide conjugated to a polypeptide.

17. A method of producing a microparticle composition, the method comprising: (a) forming microparticles by a surfactant-free emulsification process, the microparticles comprising a polymer selected from the group consisting of a poly(α-hydroxy acid), a polyhydroxy butyric acid, a polycaprolactone, a polyorthoester, a polyanhydride, and a polycyanoacrylate; and (b) adsorbing a polypeptide-containing molecule on the surface of the microparticles to form the microparticle composition.

18. The method of claim 17, wherein the emulsification process comprises: (a) forming an emulsion comprising an organic solvent, water and the polymer; and (b) removing the organic solvent from the emulsion to form microparticles.

19. The method of claim 18, wherein the emulsion is a water-in-oil-in-water emulsion that is formed by a process comprising: (a) emulsifying an organic phase comprising the polymer and the organic solvent with a first aqueous phase comprising water to form a water-in-oil emulsion; and (b) emulsifying a second aqueous phase comprising water with the emulsion formed in step (a) to form a water-in-oil-in-water emulsion.

20. The method of claim 19, wherein the emulsifying steps are conducted in a high-shear homogenizer.

21. The method of any of claims 17-20, wherein the polymer is a poly(α-hydroxy acid).

22. The method of any of claims 17-20, wherein the polymer is a poly(D,L-lactide-co-glycolide).

23. The method of claim 22, wherein the poly(D,L-lactide-co-glycolide) has a lactide/glycolide molar ratio ranging from 25:75 to 75:25 and a molecular weight ranging from 10,000 to 100,000 Daltons.

24. The method of claim 22, wherein the polymer is a poly(D,L-lactide-co-glycolide) having a lactide/glycolide molar ratio ranging from 40:60 to 60:40 and a molecular weight ranging from 20,000 Daltons to 70,000 Daltons.

25. The method of any of claims 17-20, wherein the polypeptide-containing molecule is an antigen.

26. The method of claim 25, wherein the antigen is selected from HIV antigens, meningitis B antigens, streptococcus antigens, hepatitis B virus antigens, hepatitis C virus antigens, *Haemophilus influenza* type B antigens, pertussis antigens, diphtheria antigens, tetanus antigens, *Helicobacter pylori* antigens and Influenza A hemagglutinin antigens.

27. The method of claim 25, wherein the antigen is selected from the group consisting of HIV gp41 antigen, HIV gp120 antigen, HIV gp140 antigen, HIV p24gag antigen, HIV p55gag antigen, meningitis B recombinant protein 287 antigen, and group B streptococcus antigen.

28. A microparticle composition formed by a process comprising: (a) forming microparticles by a surfactant-free emulsification process, the microparticles comprising a polymer selected from the group consisting of a poly(α-hydroxy acid), a polyhydroxy butyric acid, a polycaprolactone, a polyorthoester, a polyanhydride, and a polycyanoacrylate; and (b) adsorbing a polypeptide-containing molecule on the surface of the microparticles to form the microparticle composition.

29. The method of any of claims 17-20, wherein a weight-to-weight ratio of the adsorbed polypeptide-containing molecule to the polymer ranges between 0.001:1 and 0.1:1.

30. The microparticle composition of any of claims 1-6, and 10-13, wherein a weight-to-weight ratio of the adsorbed polypeptide-containing molecule to the polymer ranges between 0.01:1 and 0.05:1.

31. The microparticle composition of claim 28, wherein the polymer comprises a poly(α-hydroxy acid).

32. The microparticle composition of claim 31, wherein the poly(α-hydroxy acid) is selected from the group consisting of poly(L-lactide), poly(D,L-lactide) and poly(D,L-lactide-co-glycolide).

33. The microparticle composition of claim 28, wherein the polypeptide-containing molecule is an antigen.

34. The microparticle composition of claim 33, wherein the antigen is selected from HIV antigens, meningitis B antigens, streptococcus antigens, hepatitis B virus antigens, hepatitis C virus antigens, *Haemophilus influenza* type B antigens, pertussis antigens, diphtheria antigens, tetanus antigens, *Helicobacter pylori* antigens and Influenza A hemagglutinin antigens.

35. The microparticle composition of claim 33, wherein the antigen is selected from the group consisting of HIV gp41 antigen, HIV gp120 antigen, HIV gp140 antigen, HIV p24gag antigen, HIV p55gag antigen, meningitis B recombinant protein 287 antigen, and group B streptococcus antigen.

36. The microparticle composition of claim 28, further comprising an additional biologically active macromolecule selected from the group consisting of a polynucleotide, a polynucleoside, a pharmaceutical, a hormone, an enzyme, a transcription or translation mediator, an intermediate in a metabolic pathway, an immunomodulator, and an adjuvant.

37. The microparticle composition of claim 36, wherein the additional biologically active macromolecule is an adjuvant.

38. The microparticle composition of claim 37, wherein the adjuvant is a member selected from the group consisting of CpG oligonucleotides, double-stranded RNA adjuvants, aminoalkyl glucosaminide 4-phosphate adjuvants, imidazoquinoline adjuvants, lipopolysaccharide mimetic adjuvants, saponin adjuvants, *E. coli* heat-labile toxin adjuvants, monophosphorylipid A adjuvants and aluminum salts.

39. The microparticle composition of claim 28, wherein the emulsification process comprises: (a) forming an emulsion comprising an organic solvent, water and the polymer; and (b) removing the organic solvent from the emulsion to form microparticles.

40. The microparticle composition of claim 39, wherein the emulsion is a water-in-oil-in-water emulsion that is formed by a process comprising: (a) emulsifying an organic phase comprising the polymer and the organic solvent with a first aqueous phase comprising water to form a water-in-oil emulsion; and (b) emulsifying a second aqueous phase comprising water with the emulsion formed in step (a) to form a water-in-oil-in-water emulsion.

41. The microparticle composition of claim 40, wherein the emulsifying steps are conducted in a homogenizer.

* * * * *